(12) United States Patent
Beall

(10) Patent No.: US 7,025,972 B2
(45) Date of Patent: Apr. 11, 2006

(54) ALLERGEN ABSORBENT, BLOCKING, AND DEACTIVATING COMPOSITIONS AND METHOD

(76) Inventor: Gary W. Beall, 1137 Birchgate Trail, Ferguson, MO (US) 63135

( * ) Notice: Subject to any disclaimer, the term of this patent is extended or adjusted under 35 U.S.C. 154(b) by 548 days.

(21) Appl. No.: 09/867,813

(22) Filed: May 30, 2001

(65) Prior Publication Data

US 2003/0012800 A1   Jan. 16, 2003

(51) Int. Cl.
  *A61K 39/35*   (2006.01)
  *A61K 7/00*    (2006.01)
  *A01N 25/34*   (2006.01)
  *A01N 25/00*   (2006.01)

(52) U.S. Cl. .................. 424/275.1; 424/401; 424/402; 514/946; 514/947

(58) Field of Classification Search ............... 424/401, 424/402, 275.1; 514/506, 553, 675, 693, 514/715, 724, 762, 782, 844, 946, 947; 414/401
See application file for complete search history.

(56) References Cited

U.S. PATENT DOCUMENTS

| | | | |
|---|---|---|---|
| 2,531,427 A | 11/1950 | Hauser | 260/448 |
| 4,861,584 A | 8/1989 | Powell, Jr. et al. | 424/79 |
| 4,875,762 A * | 10/1989 | Kato et al. | 350/357 |
| 5,552,469 A | 9/1996 | Beall et al. | 524/445 |
| 5,578,672 A | 11/1996 | Beall et al. | 524/446 |
| 5,698,624 A | 12/1997 | Beall et al. | 524/445 |
| 5,721,306 A | 2/1998 | Tsipursky | 524/449 |
| 5,730,996 A | 3/1998 | Beall et al. | 424/405 |
| 5,760,121 A | 6/1998 | Beall et al. | 524/450 |
| 5,804,613 A | 9/1998 | Beall et al. | 523/200 |
| 5,830,528 A | 11/1998 | Beall et al. | 427/220 |
| 5,837,763 A | 11/1998 | Ferraro et al. | 524/449 |
| 5,844,032 A | 12/1998 | Serrano et al. | 524/445 |
| 5,849,830 A | 12/1998 | Tsipursky et al. | 524/450 |
| 5,877,248 A | 3/1999 | Beall et al. | 524/450 |
| 5,880,197 A | 3/1999 | Beall et al. | 524/445 |
| 5,952,095 A | 9/1999 | Beall et al. | 428/332 |
| 5,955,094 A | 9/1999 | Beall et al. | 424/405 |
| 5,998,528 A | 12/1999 | Tsipursky et al. | 524/445 |
| 6,057,396 A | 5/2000 | Lan et al. | 524/445 |
| 6,090,734 A | 7/2000 | Tsipursky et al. | 501/141 |

FOREIGN PATENT DOCUMENTS

EP   846661   *   6/1998

OTHER PUBLICATIONS

Kligman (*AMA Archives of Dermatology*), vol. 77, Feb. 1958, p. 149, et.seq.
Majima (*Ber. Deutsch Chem. Ges.*) 40:4390, 1907 and 50:172, 1922.
McNair (*J. Am. Chem. Soc.*) 43:159, 1921.
Hill, et al. (*J. Am. Chem. Soc.*) 56:2736, 1934.
Gosselin, et al., *Clinical Toxicology of Commercial Products*, 5th Edition, Williams & Walkins, 1984, PV-633.
"Final Report on the Safety Assessment of Quaternium-18, Quaternium-18 Hectorite and Quaternium-18 Bentonite", Journal of the American College of Toxicology, vol. 1(2), 1982, pp. 71-83.

* cited by examiner

Primary Examiner—Alton Pryor
(74) Attorney, Agent, or Firm—Marshall, Gerstein & Borun LLP

(57) ABSTRACT

An allergen and blocking sorbent for topical application to the skin comprising a surface-modified layered material, such as an intercalated clay, dispersed in a cosmetically acceptable solvent. The organic surface modifier is an organic molecule that contains a substantial dipole moment sufficient to bond, through ion-dipole interactions, with an exchangeable cation on the inner surface of adjacent clay platelets. Suitable organic surface modifiers include aldehydes, ketones, carboxylic acids, alcohols, phenols, ethers, catecols, lactams, lactones and pyrrolidones. The preferred layered material useful in this invention includes the entire family of smectite type clays. The composition is topically applied to the skin to absorb or adsorb (hereinafter "sorb" or "sorbent") via intercalation between spaced layers of the layered material, and block allergenic organic compounds from plants such as poison ivy, poison oak, and poison sumac, thus preventing skin rashes.

36 Claims, 6 Drawing Sheets

ALLERGEN ABSORBENT, BLOCKING, AND DEACTIVATING COMPOSITIONS AND METHOD

FIELD OF THE INVENTION

An allergen and blocking sorbent for topical application to the skin comprising a surface-modified layered material, such as an intercalated clay, dispersed in a cosmetically acceptable solvent. The organic surface modifier is an organic molecule that contains a substantial dipole moment sufficient to bond, through ion-dipole interactions, with an exchangeable cation on the inner surface of adjacent clay platelets. Suitable organic surface modifiers include aldehydes, ketones, carboxylic acids, alcohols, phenols, ethers, catecols, lactams, lactones and pyrrolidones. The preferred layered material useful in this invention includes the entire family of smectite type clays. The composition is topically applied to the skin to absorb and/or adsorb (hereinafter "sorb" or "sorbent") via intercalation between spaced layers of the layered material, and block allergenic organic compounds from plants such as poison ivy, poison oak, and poison sumac, thus preventing skin rashes.

This invention relates to an allergen sorbent and blocking composition and method for topical application to the skin to prevent or alleviate allergic skin reactions and associated skin itching of persons due to contact with poison ivy, poison oak or poison sumac.

BACKGROUND OF THE INVENTION AND PRIOR ART

Poison ivy and poison oak are two of the major causes of allergic contact dermatitis in the United States today. According to Dr. William Epstein, as reported in the Smithsonian, Volume 16, Number 5, dated August, 1985 by Noel Vietmeyer:

"Poison ivy and oak are by far the major causes of allergic contact dermatitis in the United States. More people suffer from them than from all other allergic skin diseases combined . . . No one counts the number of cases, but there are probably at least ten million a year, nationwide. Poison oak and poison ivy are possibly the greatest cause to workmen's disability in the nation: each year may bring more than 140,000 cases in the workplace, causing perhaps more than 152,000 lost work days."

According to Kligman (*AMA Arhives of Dermatology*, Vol. 77, February 1958, p. 149, et seq.,) the first significant advance in Rhus biochemistry was made by Majima (Ber. Deutsch Chem. Ges. 40:4390, 1907 and 50:172, 1922), working with urushiol. Urushiol is a yellow oil extracted from the Japanese lac tree. Later, McNair (J. Am. Chem. Soc. 43:159, 1921), studied poison oak and concluded that the active principle (lobinol) was a catechol with an unsaturated side chain, whose position and structure were not identified. Hill and his collaborators (J. Am. Chem. Soc. 56:2736, 1934) later hydrogenated poison ivy urushiol. They obtained a product identical with Majima's hydrourushiol from Japanese lac. They therefore wrongly concluded that the antigenic compounds in the American and Japanese plants were identical.

According to Kligman, however:

"The sole chemical difference between Japanese lac and poison ivy is the position of one of the unsaturated bonds of the triolefin."

Strangely, however, the allergen urushiol does not appear to affect animals and household pets. Cats and dogs can be exposed and actually play in the area without being affected, but can infect their owners by brushing up against their skin and transferring the urushiol on their coats to the unexposed areas of the human anatomy. According to Dr. Epstein, Ibid.:

"Between 15 and 25% of us are essentially immune, 25% are mildly sensitive and don't normally develop severe reactions, 25 to 30% are moderately sensitive and break out significantly with the amount of urushiol found in one leaf and 10 to 20% are so exquisitely sensitive that less than one leaf products intense dermatitis . . . ."

The oily substance urushiol, when in contact with the skin, penetrates the outer skin layers and begins to chemically bind to the skin cells. The body sees the combination of the urushiol in chemical combination with a skin cell as a foreign intruder. The immune system immediately rushes large white cells called macrophages and T-lymphocytes to destroy the affected skin cells. Dr. Epstein explains, Ibid:

"It's the body's own over-reaction that causes the complications. In sensitized persons, the area fills up with the white blood cells and they release so much cell-destroying toxins that they tear apart even the skin itself. That's what produces the blisters and suppurating sores."

Many folk remedies have been proposed for use after contact with urushiol. These include morphine (topically), bromine, kerosene, gun powder, iodine, aqua regia, buttermilk, cream and marshmallows. Additionally, innumerable botanicals, such as snake root, coffee, gelisium, hellebore, ipecac, lobelia, mustard, opium, stryhnine, veratrum, etc. have been suggested.

A major problem associated with skin contact with urushiol from poison oak, poison sumac and poison ivy is encountered by the foresters of the U.S. Forestry Service. This is particularly severe in the case of forest fires, where the soot and gases from the burning flames contain urushiol, which can get onto the foresters fighting the fire and even into their respiratory system. This is further complicated by the fact that the urushiol coats formites, such as clothing, utensils, even carbon and soot in the area of forest fires and can therefore provide another method of contact, even outside the area of the plants themselves.

Dr. Edward E. Waali, working under contract with the U.S. Forestry Service, tested many materials in an effort to find a chemical which would absorb or somehow chemically bind urushiol. Waali tested solid absorbents, such as silica gel, alumina and activated charcoal. Additionally, he saturated samples of cloth and mordanted them with salts of aluminum, copper and chromium.

Dr. William L. Epstein, also working under contract with the U.S. Forestry Service, became aware of Dr. Waali's work and tested a wide variety of agents, including Sure® antiperspirant and Drysol™, both of which contain the antiperspirant aluminum chlorohydrate. The Sure® antiperspirant, in the spray form, contains aluminum chlorohydrate, cyclomethicone, quaternium-18 hectorite, perfume, ethanol, isobutane and propane. This composition is reported from 1 to 5% quaternium-18 hectorite, an onium (equaternary ammonium) ion-exchanged hectorite clay. See for example, *Clinical Toxicology of Commercial Products*, Gosselin, et al., 5th edition, William and Watkins, 1984, PV-633.

Quaternium-18 hectorite is a reaction product of hectorite and quaternium-18 and is commercially available as Bentone 38 (NL Chemicals). Quaternium-18 (CAS Number 61789-80-8) is predominantly (90 to 100%) a quaternary salt that conforms generally to the formula:

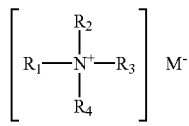

wherein $R_1$ and $R_2$ represent hydrogenated tallow fatty radicals, $R_3$ and $R_4$ are methyl groups, and $M^-$ is a halide, acetate or hydroxide anion. It is well known that onium ions, e.g., quaternary ammonium ions, react with layered clay materials, such as hectorite, by ion-exchange of the positively charged nitrogen atom exchanging with exchangeable cations on the inner surfaces of the clay platelets. Such onium ion-exchanged clays, while being somewhat effective to sorb urushiol, have a relatively low capacity for urushiol sorption in comparison to the layered materials of the present invention.

Quaternium-18, quaternium-18 hectorite and quaternium-18 bentonite are organophilic clays that are generally considered safe as cosmetic ingredients and have been widely used as suspending agents for antiperspirants. See "Final Report on the Safety Assessment of Quaternium-18, Quaternium-18 Hectorite and Quaternium-18 Bentonite," *Journal of the American College of Toxicology*, Vol. 1(2), 1982, pp. 71–83.

Accordingly, a need has continued to exist for an effective and cosmetically acceptable material to protect humans from the effects of skin contact with poison ivy and similar poisonous plants.

In 1989 Powell et al. patented an aerosol composition of organophilic clay dispersed in a cosmetically acceptable solvent (U.S. Pat. No. 4,861,584). This composition suffers from several drawbacks that include high cost, drying of the skin, allergic reaction in some individuals to quaternary ammonium compounds, relatively low sorption capacity for urushiol, incompatibility with most common cosmetically acceptable solvents, weak bonding of urushiol to the organophilic clay, and the need for polar activators, such as low molecular weight alcohols or ketones.

SUMMARY OF THE INVENTION

This invention overcomes at least some of the drawbacks of the previous invention with improved efficacy. The composition of the present invention includes a surface modified clay and a composition of the surface modified clay dispersed in a cosmetically acceptable solvent for topical application to skin to prevent or alleviate allergic skin reactions from exposure to urushiol. The organic surface modifying agent is an organic molecule that has a substantial dipole moment, greater than the dipole moment of water, and/or includes one or more groups or moieties that contain partial negative charges. Such molecules are typified by organic monomers, oligomers and polymers such as aldehydes, ketones, carboxylic acids, ethers, alcohols, phenols, catechols, lactones, lactams, amides, esters, and pyrrolidones. FIG. 1 shows a molecule of dodecylpyrrolidone (3) and a molecule of urushiol (2) bonding to a sodium ion (1) through ion-dipole bonding. The clay surface has been omitted for clarity.

The layered materials useful in the compositions and methods of the present invention, preferably a clay, e.g., a smectite clay, preferably include any of the smectite type clays. Specific minerals useful in this invention include montmorillonite, hectorite, saponite, beidellite, and stevensite. These smectite clays can also be synthesized hydrothermally by forming an aqueous reaction mixture in the form of a slurry containing mixed hydrous oxides or hydroxides of the metals with or without, as the case may be, sodium (or alternate exchangeable cation mixtures thereof) fluoride in the proportions defined by the formula for the smectite desired. The slurry is then placed in an autoclave and heated under autogenous pressure to a temperature within the range of approximately 100 to 325 degrees centigrade for a sufficient time to form the desired product.

The clay is intercalated with the organic surface modifier easily by mixing the surface modifier, e.g., dodecylpyrrolidone, with the clay in a mechanical mixer, such as a pug mill or Z-blade mixer. The concentration of the organic surface modifier can vary from about 2% by weight to about 90% by weight, preferably about 10% by weight to about 50% by weight, based on the dry weight of the clay. Preferably, the clay includes at least about 4% by weight water for initial, limited clay platelet separation, or water can be added to the clay prior to or during intercalation of the clay with the organic surface modifier. The organic surface modifier is introduced into the layered material galleries in the form of a liquid composition (with or without water) having a surface modifier concentration sufficient to provide a concentration of at least about 2%, preferably about 10% to about 50% by weight surface modifier, based on the dry weight of the clay, preferably at a molar ratio of surface modifier to exchangeable clay interlayer cations of at least about 0.5:1, more preferably at least about 1:1, particularly at least about 1.5:1, and most preferably at least about 2:1, up to about 5:1, e.g., particularly in the range of about 2:1 to about 3:1.

According to this invention the surface modified clay dispersed in a cosmetically acceptable solvent is applied to the skin, for sorption of urushiol, to prevent or reduce skin contact with urushiol, thereby effectively blocking or reducing the allergic reaction caused by exposure to urushiol. The intercalated sorbent of the present invention acts to sorb and deactivate the urushiol in three ways. First, due to the plate-like structure of the clay, it forms a physical barrier on the skin since the clay platelets align themselves parallel to the skin. Secondly, the surface modifier intercalated between the clay platelets sorbs the urushiol through Van der Waals-type attraction. Thirdly, the catechol portion of the urushiol molecule displaces some of the surface modifier and bonds, via ion-dipole attraction, to an exchangeable cation on the clay platelet inner surface, displacing a portion of the ion-dipole bonded surface modifier. This third part of the mechanism, wherein the urushiol displaces the surface modifier and is bonded to inner platelet cations, and is retained between the clay platelets of the intercalate, completely deactivates the urushiol, and encases the urushiol to prevent further skin contact.

Accordingly, an object of this invention is to provide a skin protecting composition.

A further object of the invention is to provide protection from urushiol-containing plants such as poison ivy, poison oak, and poison sumac.

DETAILED DESCRIPTION OF THE PREFERRED EMBODIMENT

The surface modification of clays utilizing an ion-exchange reaction with quaternary ammonium (onium) compounds are well known (Hauser U.S. Pat. No. 2,531,427). Others have disclosed intercalating clays with organic spacing molecules for easier exfoliation so that the exfoliated platelets can be mixed with polymers for improved strength, temperature resistance, and oxygen barrier properties in the polymer (see, for example, U.S. Pat. Nos. 5,552,469; 5,578,672; 5,698,624; 5,721,306; 5,730,996; 5,760,121; 5,804,613; 5,830,528; 5,837,763; 5,844,032; 5,849,830; 5,877,248; 5,880,197; 5,952,095; 5,955,094; 5,998,528 and 6,057,396.

Figure 1:
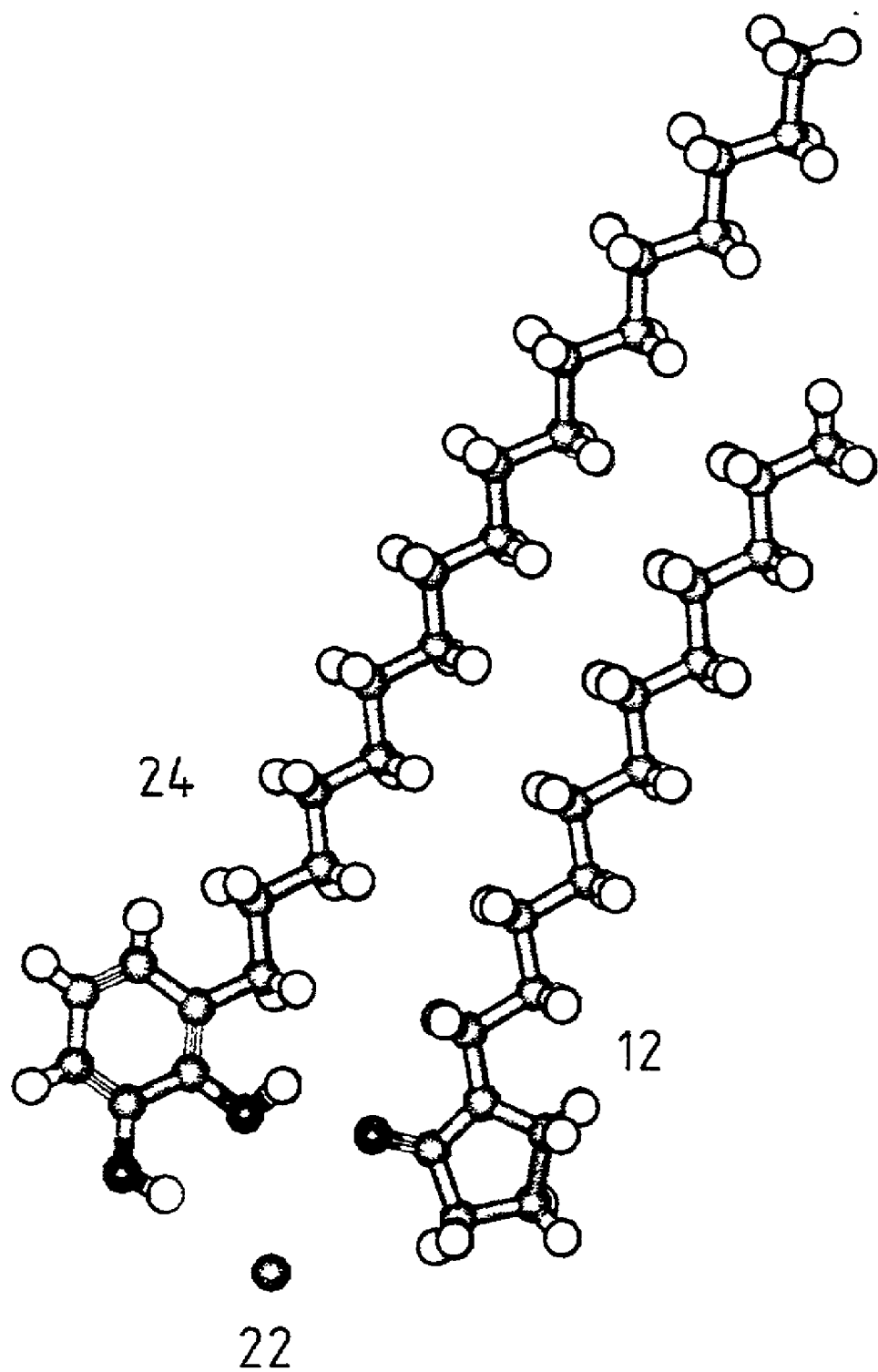
FIG. 1 is a diagram illustrating ion-dipole bonding of surface modifiers to a cation of a clay platelet surface.

In accordance with the present invention, the clay inner platelet surface is intercalated with one or more organic molecules that possesses a dipole moment greater than that of water, or has groups that contain partial negative charges. These polar organic compounds bond to the clay inner surface at inner surface cation sites by ion-dipole interaction between the partial negative charge on the organic molecule and the clay inner platelet exchangeable cation (FIG. 1). Typical organic surface modifiers include aldehydes, ketones, carboxylic acids, alcohols, phenols, esters, catecols, lactams, lactones and pyrrolidones. The organics that are most preferred include n-alkyl pyrrolidones, polyvinyl pyrrolidone, copolymers of vinyl pyrrolidone, vinyl alcohol, with a long chain ($C_6$–$C_{24}$) vinyl alkyl group, or mixtures thereof. The preferred alkyl groups are generally $C_{10}$ to $C_{22}$ in length, preferably $C_{12}$ (dodecyl). The n-alkyl pyrrolidones are the most preferred surface modifiers for intercalation between the clay platelets.

Figure 2:
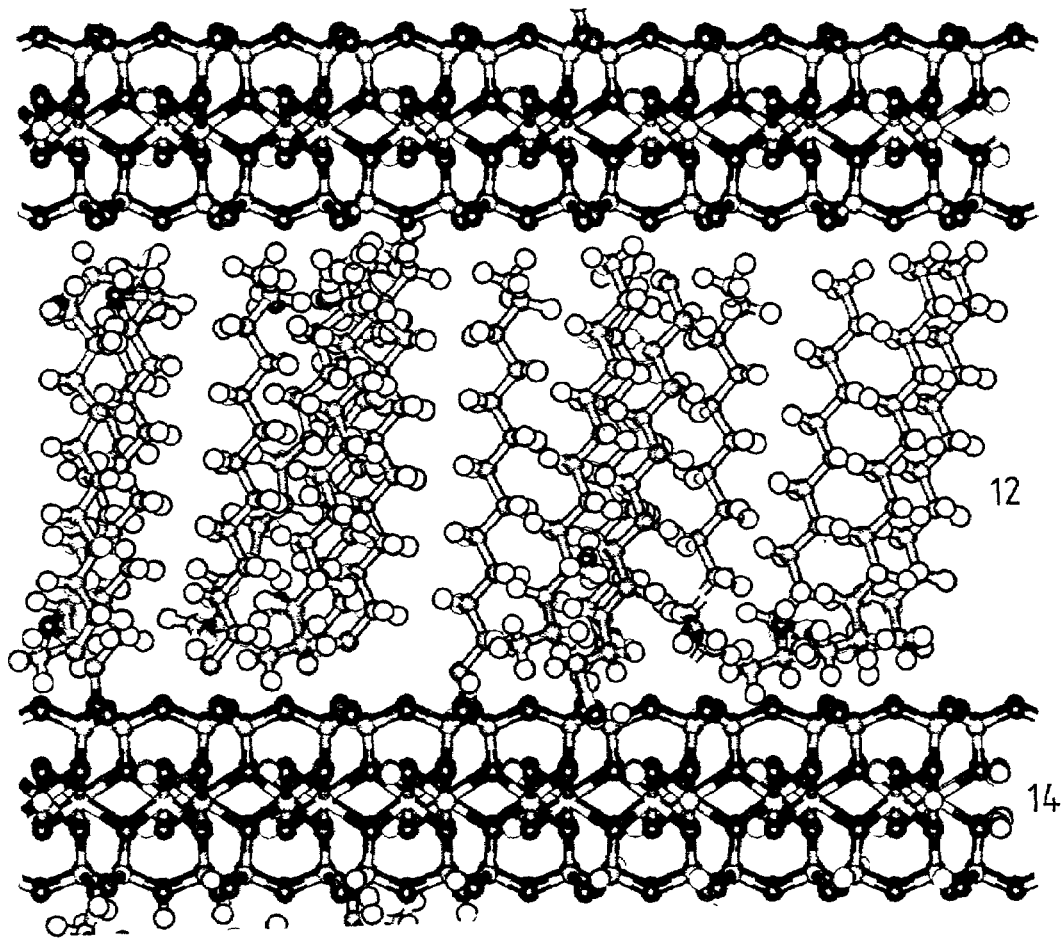
FIG. 2 is a diagram illustrating the structure of a conventional organoclay, intercalated with a conventional onium ion organic surface modifier.
Figure 3:
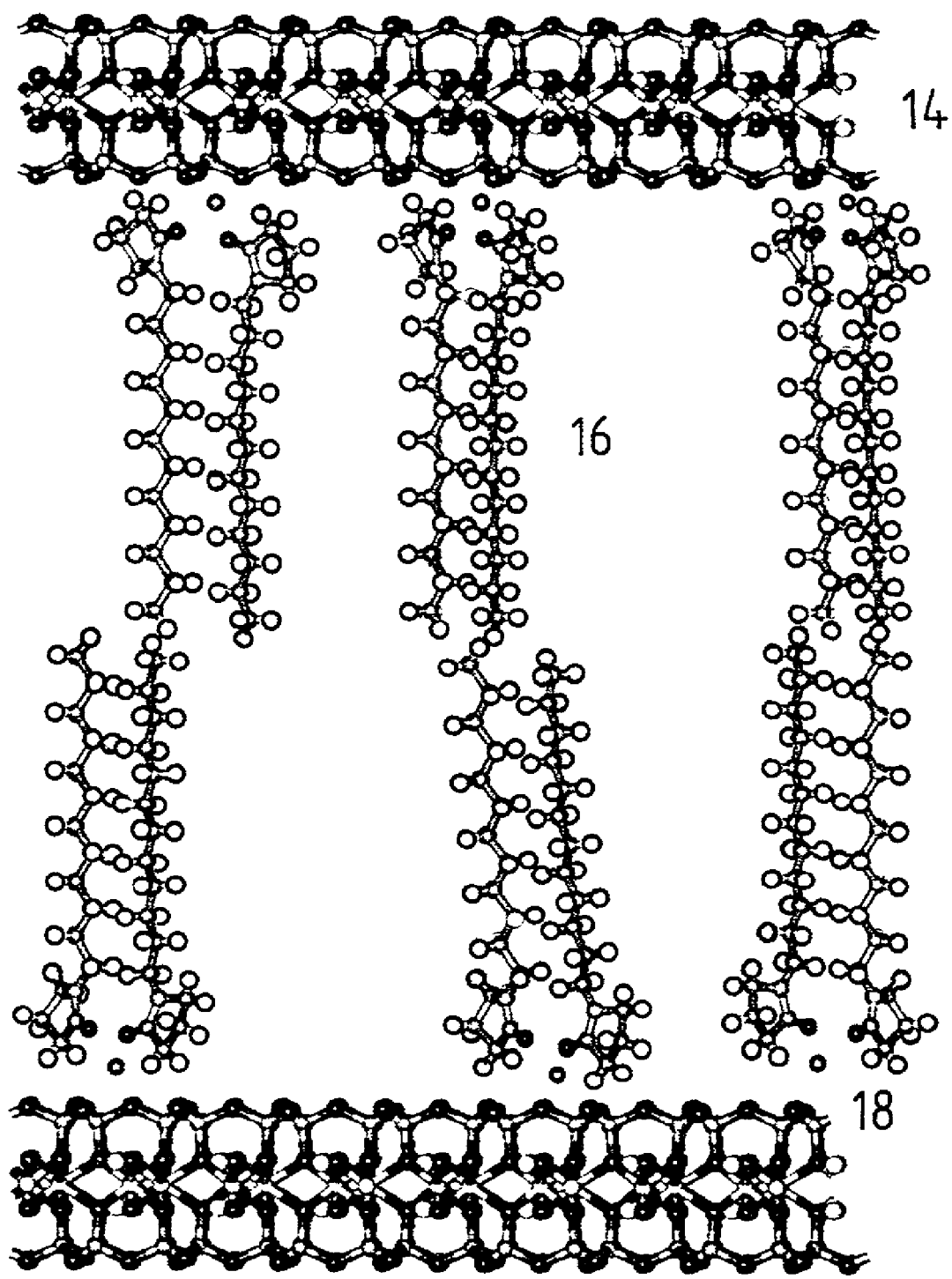
FIG. 3 is a diagram illustrating the structure of an ion-dipole bonded surface modified clay.

In particular, the long chain surface modifiers that do not provide onium ions upon dissolution, and therefore do not ion-exchange with inner platelet cations, e.g., dodecylpyrrolidone (DDP), form a unique structure that is quite different from traditional ion-exchanged or covalently reacted organophilic clays. Traditional organoclays form a structure, as shown in FIG. 2, where the dodecylammonium cation 12 has been ion-exchanged onto the surface of the clay 14. The dodecylammonium molecules from opposite clay platelets will interdigitate and form a structure that is very dense between the platelets, allowing relatively little sorption (intercalation) of other molecules, and will exhibit a space between the platelets of only about 12 Angstroms (Å). The polar surface modifiers of the present invention, e.g., DDP, coordinate by ion-dipole attraction to the exchangeable cations on the inner surface of the clay platelets through, for example, the carbonyl on the pyrrolidone ring. With a 1:1 molar ratio of DDP to clay inner surface cations, the DDP $C_{12}$ alkyl groups can interact with ion-dipole bonded alkyl groups extending inwardly from an inner surface of an adjacent clay platelet to form a high density structure similar to that in traditional organoclays. However, as shown in FIG. 3, when the molar ratio of the surface modifier to clay inner platelet cations approaches 2:1 the alkyl groups of the opposed two DDP molecules 12 extending inwardly from opposite clay platelet surfaces self assemble into a rigid structure. Since the cations 18 that the DDP molecules are ion-dipole coordinated to are randomly distributed on the clay surface 14, these rigid structures cannot intermesh any longer. The resulting structure is very open (significantly more spacing between adjacent inner clay platelet surfaces) and can sorb and retain substantially more urushiol.

Sufficient surface modifier should be bonded to the clay platelet surfaces by ion-dipole bonding to make the clay hydrophobic. It should be understood, however, that up to 50%, preferably no more than 25% of the ion-exchange sites on the inner platelet surfaces can be ion-exchanged with onium ions, while achieving added sorption of urushiol in accordance with the present invention.

The preferred clays for making the sorbent of the present invention are of the smectite-type clays. Specific minerals useful in this invention include montmorillonite, hectorite, saponite, beidellite, and stevensite. These smectite clays can also be synthesized hydrothermally by forming an aqueous reaction mixture in the form of a slurry containing mixed hydrous oxides or hydroxides of the metals with or without, as the case may be, sodium (or alternate exchangeable cation or mixtures thereof) fluoride in the proportions defined by the formula for the smectite desired, as described in U.S. Pat. No. 6,090,734, issued Jul. 18, 2000, hereby incorporated by reference. The slurry is then placed in an autoclave and heated under autogenous pressure to a temperature within the range of approximately 100 to 325 degrees centigrade for a sufficient time to form the desired product. The most preferred mineral is montmorillonite. The preferred exchangeable cation is sodium and the clay should have a cation exchange capacity of between about 75 and about 150 milliequivalents per 100 grams of clay.

The manufacture of the allergen sorbent of the present invention is easily accomplished by mixing the surface modifier, e.g., DDP, directly with the clay in a mechanical mixer such as a pug mill or Z-blade mixer. The resultant mixture is then dried and pulverized. This process is superior to that utilized to make organoclays. The prior art organoclay process requires dispersion of the clay and quaternary ammonium compound at low concentrations in water, normally less than 5% by weight quaternary ammonium compound, mixing of the two slurries to facilitate ion-exchange, subsequent filtering, drying, and sizing. The ion-exchange reaction leaves a substantial amount of by-product salt in the finished organoclay. This salt leads to corrosion of processing equipment and aerosol containers used for packaging. The process for making the allergen sorbent of the present invention produces essentially no by-products that remain in the resulting surface-modified clay.

The thus produced surface-modified clay is then dispersed in a cosmetically acceptable solvent. Examples of cosmetically-acceptable solvents include those disclosed in the Powell et al. U.S. Pat. No. 4,861,584, hereby incorporated by reference, and include volatile silicon, triglycerides, glycerol, and ethanol. The clay is normally dispersed using high speed mixers or colloid mills that are well known in the art. The surface modified clay is most useful as an intercalate or as tactoids of intercalates, or can be fully dispersed, by high shear mixing such that at least 80%, at least 90%, or up to 100% of the surface modifier-intercalated clay particles are exfoliated down to the individual clay platelets in order to achieve a complete coating of surface modified clay on the skin, which is best as a preventative measure, as opposed to the intercalate being better for treatment of urushiol-contacted skin.

This surface modified clay in a dispersion or gel can be applied to the skin as a salve or as an aerosol spray. When applying to the skin, the optimum results are obtained by rubbing the sorbent composition topically onto the skin. The rubbing action orients the clay platelets parallel to the skin surface, thus providing the maximum physical barrier properties.

The preferred concentrations for the surface-modified clay in the sorbent composition should be in the range of 1% to about 25% by weight. A more preferred range is about 5% to about 15% surface-modified clay.

Figure 4:
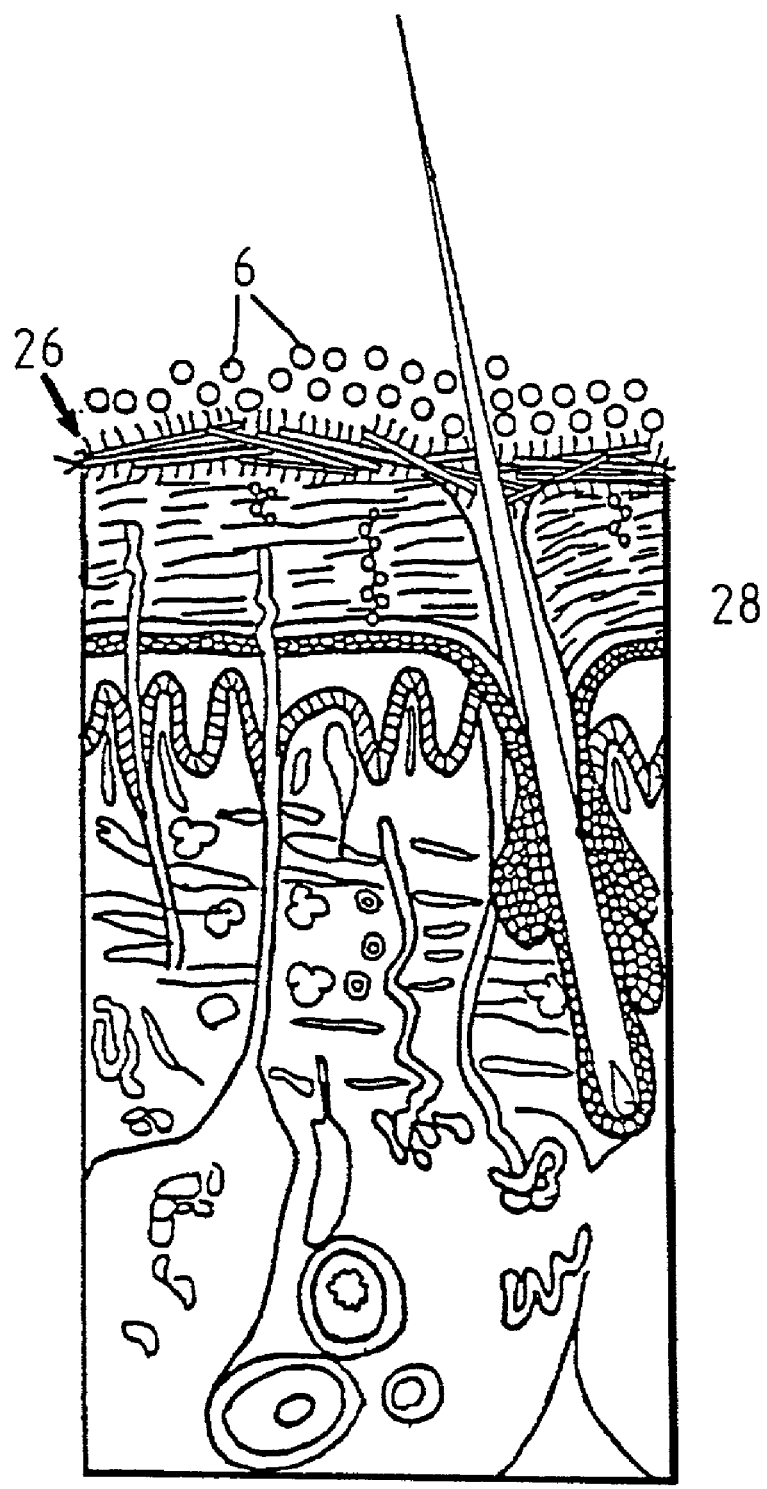
FIG. 4 is a diagram illustrating the physical barrier formed by the surface modified clay on the skin.
Figure 5:
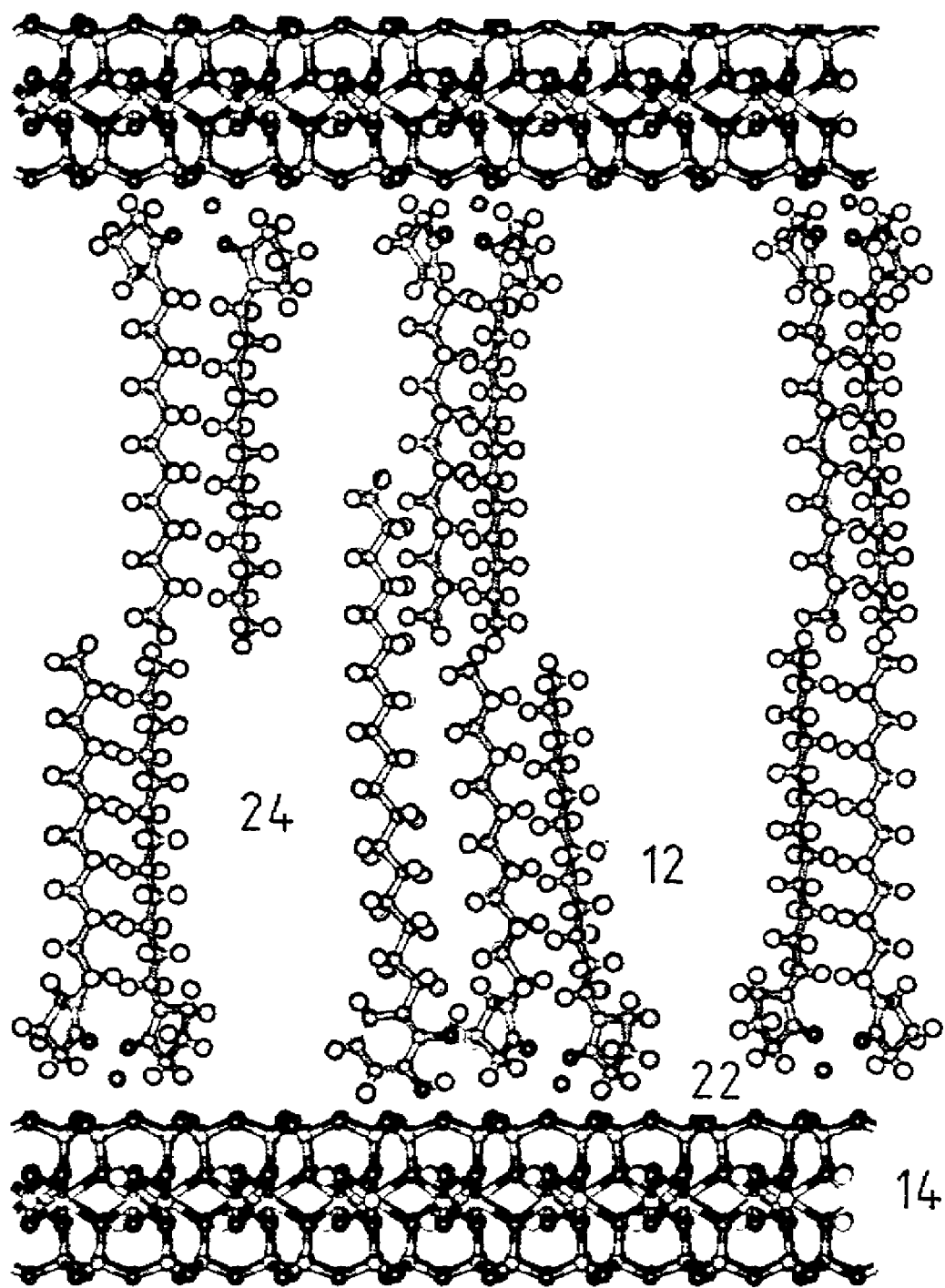
FIG. 5 is a diagram illustrating the initial sorption of a urushiol molecule via Van der Waals forces.
Figure 6:
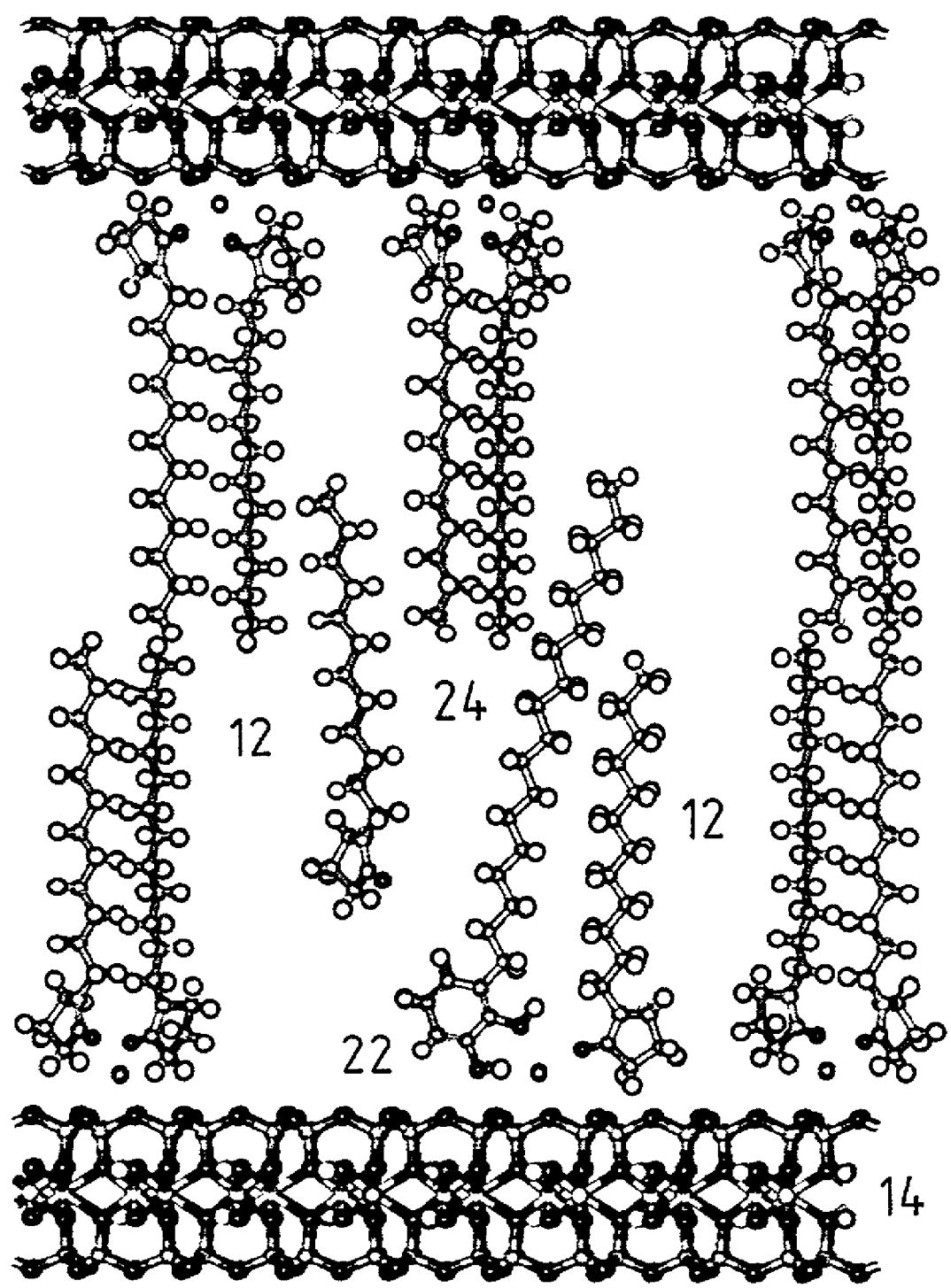
FIG. 6 is a diagram illustrating the displacement of a dodecylpyrrolidone surface modifier molecule by a urushiol molecule, thus deactivating the urushiol due to ion-dipole bonding of the urushiol molecule to the sodium on the clay platelet surface.

The invention has a three-fold mechanism of protecting the skin from the urushiol. This is in contrast to traditional organoclays where the only mechanism of sorption is one of Van der Waals attraction. The first mechanism for the composition of the present invention is illustrated in FIG. 4, wherein the formation of physical barrier is achieved by orienting individual clay platelet surfaces 12 parallel to the surface of the skin 20, thus shielding the skin from urushiol 6. Secondly, as shown in FIG. 5, the alkyl groups of the surface modifier, e.g., dodecylpyrrolidone 12 bonded to the sodium cation 22 on the clay surface 14 sorbs the urushiol 24 through Van der Waals attractions. Thirdly, as shown in FIG. 6, the urushiol 24 subsequently bonds, via ion-dipole attraction, to exchangeable cations 22 by displacing some of the surface modifier 12, thereby completely deactivating the urushiol.

FIG. 1 illustrates the ion-dipole electrostatic attraction or bonding between a sodium exchangeable cation 22 on an inner clay platelet surface 12, urushiol 24 and dodecylpyrrolidone 12. FIG. 2 illustrates the structure of a conventional organoclay surface 14. The clay 14 has been ion-exchanged with dodecyl ammonium 25 to form a dense interdigitated structure with a gallery spacing of about 12 Angstroms. FIG. 3 illustrates the structure of an ion-dipole bonded surface modified clay. The sodium exchangeable cation 22 is bonded to two dodecylpyrrolidone (DDP) molecules 12 on the clay surface 14. This yields a very open structure since the DDP molecules self-assemble into a rigid structure that cannot be interdigitated. This structure gives a gallery spacing of about 35 Angstroms. FIG. 4 illustrates the protective physical barrier formed by the clay platelets 26 as they lie parallel to the skin surface 28, thus stopping contact of urushiol 24 with the skin. FIG. 5 illustrates that a urushiol molecule 24 first bonds via Van der Waal forces to the alkyl chain of the DDP 12 that is ion-dipole bonded to the sodium 22 on the clay platelet surface 12. FIG. 6 illustrates the urushiol molecule 24 bonding to the sodium ion 22 and displacing one of the DDP molecules 12, thus deactivating the urushiol.

EXAMPLES

Example 1

In a Hobart mixing bowl, 300 grams of montmorillonite was mixed with 120 grams of water. To this mixture 150 grams of dodecylpyrrolidone was added. The surface modified clay was then dried and ground to a 325 mesh powder.

Example 2

The surface modified clay from Example 1 was dispersed in several cosmetically acceptable solvents. A traditional organoclay utilized in Powell et al. U.S. Pat. No. 4,861,584 was also dispersed in the same solvents. Table 1 contains the results of those experiments.

| | Volatile Silicon | Glycerol | Ethanol | Caster Oil |
|---|---|---|---|---|
| Invention | Gel | Strong Gel | Gel | Gel |
| Organoclay | Poor Gel | No Gel | No Gel | Very Poor Gel |

It is clear that the sorbent of the present invention forms a gel more easily with cosmetically acceptable solvent vehicles.

Example 3

The relative bond strengths between urushiol and a traditional organoclay were compared by molecular modeling and solvent extraction. The Van der Waals forces between the urushiol and the alkyl groups of a traditional organoclay was calculated to be 16 kilocalories/mole. The interaction between the urushiol and the exchangeable cation on the clay surface of this invention was calculated to be 69 kilocalories/mole. This would indicate that the urushiol will be bound to the surface-modified clay of the present invention five times stronger than a traditional organoclay.

To experimentally verify this, one gram samples of the surface modified clay of Example 1 and a traditional organoclay were each mixed with one milligram of urushiol contained in 250 microliters of ethanol. The ethanol was evaporated from the mixtures. The remaining clay samples were then extracted with ethanol by mixing the clay samples in 20 milliters of ethanol with subsequent centrifugation to remove the clay. The supernate was then analyzed with a gas chromatograph. The urushiol recovery was 85% and 3%, respectively, for the traditional organoclay and the clay of Example 1. This is a graphic illustration of the ability of the surface-modified clay of the present invention to retain and deactivate the urushiol through the ion-dipole bonding.

What is claimed is:

1. A method for protecting skin from contact with an allergen consisting of applying to the skin an allergen sorbent composition comprising a smectite clay dispersed in a cosmetically acceptable carrier, said smectite clay having a cation exchange capacity of at least 75 meq./100 grams of clay, intercalated with an intercalant consisting of an organic surface modifier intercalant molecule that contains at least one moiety selected from the group consisting of aldehyde, ketone, carboxylic acid, alcohol, phenol, ether, catechol, lactam, lactone and pyrrolidone, said intercalant molecule being ion-dipole bonded on an inner platelet surface of the clay to form a surface-modified clay.

2. The method of claim 1, wherein the composition comprises 1% to about 30% by weight of the surface modified clay and 99% to 70% by weight solvent.

3. The method of claim 1, wherein the allergen sorbent composition is applied as a salve.

4. The method of claim 1, wherein the smectite clay is a montmorillonite clay.

5. The method of claim 1, wherein the smectite clay is a synthetic smectite.

6. A method for protecting skin from contact with an allergen by topically applying to the skin an allergen sorbent composition consisting of a smectite clay having a cation exchange capacity of at least 75 meq./00 grams of clay, intercalated with an organic surface modifier intercalant molecule that contains at least one moiety selected from the group consisting of aldehyde, ketone, carboxylic acid, alcohol, phenol, ether, catechol, lactam, lactone and pyrrolidone, said intercalant molecule being ion-dipole bonded on an inner platelet surface of the clay to form a surface-modified clay; said surface-modified clay dispersed in a cosmetically acceptable carrier selected from the group consisting of propylene glycol, ethanol, cyclomethicone, dimethicone, hexamethyldisiloxane, isopropyl palmitate, isopropyl myristate, glycerol and admixtures thereof, wherein the allergen sorbent composition is applied as an aerosol spray.

7. A method for protecting skin from contact with an allergen comprising topically applying to the skin an allergen sorbent composition comprising a smectite clay having a cation exchange capacity of at least 75 meq./100 grams of clay, intercalated with an organic surface modifier intercalant molecule that contains at least one moiety selected from the group consisting of aldehyde, ketone, carboxylic acid, alcohol, phenol, ether, catechol, lactam, lactone and pyrrolidone, said intercalant molecule being ion-dipole bonded on an inner platelet surface of the clay to form a surface-modified clay; said surface-modified clay dispersed in a cosmetically acceptable carrier selected from the group consisting of propylene glycol, ethanol, cyclomethicone, dimethicone, hexamethyldisiloxane, isopropyl palmitate, isopropyl myristate, glycerol and admixtures thereof, wherein the composition is applied to a substrate selected from the group consisting of clothing, shoes, and pets to deactivate an allergen sorbed thereon.

8. The method of claim 7, wherein the organic surface modifier is contained by the clay in an amount in the range of about 10% to about 50% by weight, based on the total weight of the surface modified clay, without considering the weight of the cosmetically acceptable carrier.

9. The method of claim 7, wherein the organic surface modifier is an n alkyl pyrrolidone wherein the alkyl is at least 10 carbon atoms in length.

10. The method of claim 7, wherein the amount of surface modified clay dispersed in the cosmetically acceptable carrier is in the range of 1% to about 30% by weight, based on the total weight of the composition.

11. The method of claim 7, wherein the amount of surface modified clay dispersed in the cosmetically acceptable carrier is in the range of about 5% to about 15% by weight, based on the total weight of the composition.

12. The method of claim 7, wherein the cosmetically acceptable carrier is selected from the group consisting of propylene glycol, ethanol, a volatile silicon fluid, isopropyl palmitate, isopropyl myristate, glycerol, and admixtures thereof.

13. The method of claim 7, wherein the smectite clay is selected from the group consisting of montmorillonite, saponite, hectorite, beidellite, and mixtures thereof.

14. A method of deactivating an allergen and reducing the severity of an allergic reaction caused by contact of the allergen with human skin comprising applying to the clothes of an individual, after exposure to said allergen, a composition comprising a smectite clay having a cation exchange capacity of at least 75 meq./100 grams of clay, intercalated with an organic surface modifier intercalant molecule to form a surface-modified clay, said intercalant molecule containing at least one moiety selected from the group consisting of aldehyde, ketone, carboxylic acid, alcohol, phenol, ether, catechol, lactam, lactone and pyrrolidone, said intercalant molecule being ion-dipole bonded on an inner platelet surface of the clay; said surface-modified clay dispersed in a cosmetically acceptable carrier.

15. An allergen sorbent composition consisting of a smectite having a cation exchange capacity of at least 75 meq./100 grams of clay, intercalated with an intercalant consisting essentially of an organic surface modifier intercalant molecule that contains at least one moiety selected from the group consisting of aldehyde, ketone, carboxylic acid, alcohol, phenol, ether, catechol, lactam, lactone and pyrrolidone, said intercalant molecule being ion-dipole bonded on an inner platelet surface of the clay to form a surface-modified clay.

16. The composition of claim 15, wherein the organic surface modifier is ion dipole bonded on the inner platelet surface of the clay in an amount in the range of about 10% to about 50% by weight, based on the total weight of the surface modified clay.

17. The composition of claim 15, wherein the organic surface modifier is an alkyl pyrrolidone, wherein the alkyl has at least 6 carbon atoms.

18. The composition of claim 15, wherein the amount of surface modified clay dispersed in the cosmetically acceptable carrier is in the range of 1% to about 30% by weight, based on the total weight of the composition.

19. The composition of claim 15, wherein the amount of surface modified clay dispersed in the cosmetically acceptable carrier is in the range of about 5% to about 15% by weight, based on the total weight of the composition.

20. An allergen sorbent composition consisting of a synthetic smectite clay dispersed in a cosmetically acceptable carrier, said smectite clay having a cation exchange capacity of at least 75 meq./100 grams of clay, intercalated with an intercalant consisting essentially of an organic surface modifier intercalant molecule that contains at least one moiety selected from the group consisting of aldehyde, ketone, carboxylic acid, alcohol, phenol, ether, catechol, lactam, lactone and pyrrolidone, said intercalant molecule being ion-dipole bonded on an inner platelet surface of the clay to form a surface-modified clay.

21. An allergen sorbent consisting of a smectite clay having a cation exchange capacity of at least 75 meq./100 grams of clay, intercalated with an intercalant consisting essentially of an alkyl pyrrolidone surface modifier intercalant molecule to form a surface-modified clay, said intercalant molecule containing a carbonyl moiety and an alkyl moiety having at least 6 carbon atoms selected from the group consisting of a carboxylic acid, a ketone, an aldehyde, a lactone, a lactam, and a pyrrolidone, said allergen sorbent being dispersed in a carrier to form an allergen sorbent composition in the form of a salve, wherein the composition comprises 1% to about 30% by weight of the allergen sorbent and 99% to 70% by weight carrier.

22. An allergen sorbent composition consisting of a smectite clay having a cation exchange capacity of at least 75 meq./100 grains of clay, intercalated with an intercalant consisting of an alkyl pyrrolidone surface modifier intercalant molecule wherein the alkyl contains at least 6 carbon atoms, said intercalant molecule being ion-dipole bonded on an inner platelet surface of the clay to form a surface-modified clay.

23. The composition of claim 22, wherein the smectite clay is a synthetic smectite.

24. A method for protecting skin from contact with an allergen consisting of topically applying to the skin an allergen sorbent composition comprising a smectite clay having a cation exchange capacity of at least 75 meq./100 grams of clay, intercalated with intercalants consisting of an organic surface modifier intercalant molecule that contains at least one moiety selected from the group consisting of aldehyde, ketone, carboxylic acid, alcohol phenol, ether, catechol, lactam, lactone, and pyrrolidone and a cosmetically acceptable carrier, said organic surface modifier intercalant molecule being ion-dipole bonded on an inner platelet surface of the clay to form a surface-modified clay; said surface-modified clay dispersed in a cosmetically acceptable carrier, wherein the allergen sorbent composition is applied as a salve.

25. The method of claim 24, wherein the surface modifier is an alkyl pyrrolidone, wherein the alkyl contains at least 6 carbon atoms.

26. A method for protecting skin from contact with an allergen by topically applying to the skin an allergen sorbent composition consisting of a smectite clay having a cation exchange capacity of at least 75 meq./100 grams of clay, intercalated with an organic surface modifier intercalant molecule that contains at least one moiety selected from the group consisting of aldehyde, ketone, carboxylic acid, alcohol phenol, ether, catechol, lactam, lactone, and pyrrolidone, said intercalant molecule being ion-dipole bonded on an inner platelet surface of the clay to form a surface-modified clay; said surface-modified clay dispersed in a cosmetically acceptable carrier, wherein the allergen sorbent composition is applied as an aerosol spray.

27. The method of claim 26, wherein the surface modifier is an alkyl pyrrolidone, wherein the alkyl contains at least 6 carbon atoms.

28. A method for protecting skin from contact with an allergen comprising topically applying to a substrate selected from the group consisting of clothing, shoes, and pets, an allergen sorbent composition comprising a smectite clay having a cation exchange capacity of at least 75 meq./100 grams of clay, intercalated with an organic surface modifier intercalant molecule that contains at least one moiety selected from the group consisting of aldehyde, ketone, carboxylic acid, alcohol phenol, ether, catechol, lactam, lactone, and pyrrolidone, said intercalant molecule being ion-dipole bonded on an inner platelet surface of the clay to form a surface-modified clay; said surface-modified clay dispersed in a cosmetically acceptable carrier and applied to deactivate the allergen sorbed on the substrate.

29. The method of claim 28, wherein the surface modifier is an alkyl pyrrolidone, wherein the alkyl contains at least 6 carbon atoms.

30. A method for protecting skin from contact with an allergen by topically applying to the skin an allergen sorbent composition consisting of a smectite clay having a cation exchange capacity of at least 75 meq./100 grams of clay, intercalated with an intercalant consisting of an organic surface modifier intercalant molecule that contains at least one moiety selected from the group consisting of aldehyde, ketone, carboxylic acid, alcohol phenol, ether, catechol, lactam, lactone, and pyrrolidone, said intercalant molecule being ion-dipole bonded on an inner platelet surface of the clay to form a surface-modified clay; said surface-modified clay dispersed in a cosmetically acceptable carrier selected from the group consisting of propylene glycol, ethanol, a volatile silicon fluid, isopropyl myristate, glycerol, and admixtures thereof.

31. The method of claim 30, wherein the surface modifier is an alkyl pyrrolidone, wherein the alkyl contains at least 6 carbon atoms.

32. A method for protecting skin from contact with an allergen by topically applying to the skin an allergen sorbent composition consisting of a synthetic smectite clay having a cation exchange capacity of at least 75 meq./100 grams of clay, intercalated with an intercalant consisting of an organic surface modifier intercalant molecule that contains at least one moiety selected from the group consisting of aldehyde, ketone, carboxylic acid, alcohol, phenol, ether, catechol, lactam, lactone and pyrrolidone, said intercalant molecule being ion-dipole bonded on an inner platelet surface of the clay to form a surface-modified clay; said surface-modified clay dispersed in a cosmetically acceptable carrier.

33. The method of claim 32, wherein the surface modifier is an alkyl pyrrolidone, wherein the alkyl contains at least 6 carbon atoms.

34. A method of deactivating an allergen and reducing the severity of an allergic reaction caused by contact of the allergen with human skin comprising applying to the allergen-exposed skin area of an individual, after exposure of said skin area to said allergen, a composition consisting of a smectite clay having a cation exchange capacity of at least 75 meq./100 grams of clay, intercalated with an intercalant consisting of an organic surface modifier intercalant molecule that contains at least one moiety selected from the group consisting of aldehyde, ketone, carboxylic acid, alcohol, phenol, ether, catechol, lactam, lactone and pyrrolidone; said intercalant molecule being ion-dipole bonded on an inner platelet surface of the clay; said clay dispersed in a cosmetically-acceptable carrier.

35. The method of claim 34, wherein the surface modifier is an alkyl pyrrolidone, wherein the alkyl contains at least 6 carbon atoms.

36. An allergen sorbent consisting of a smectite clay having a cation exchange capacity of at least 75 meq./100 grams of clay, intercalated with an alkyl pyrrolidone surface modifier intercalant molecule to form a surface-modified clay, said intercalant molecule containing a carbonyl moiety and an alkyl moiety having at least 6 carbon atoms selected from the group consisting of a carboxylic acid, a ketone, an aldehyde, a lactone, a lactam, and a pyrrolidone, said allergen sorbent being dispersed in a carrier to form an allergen sorbent composition in the form of an aerosol spray, wherein the composition comprises 1% to about 30% by weight of the allergen sorbent and 99% to 70% by weight carrier.

* * * * *

UNITED STATES PATENT AND TRADEMARK OFFICE
CERTIFICATE OF CORRECTION

PATENT NO. : 7,025,972 B2
APPLICATION NO. : 09/867813
DATED : April 11, 2006
INVENTOR(S) : Gary W. Beall It is certified that error appears in the above-identified patent and that said Letters Patent is hereby corrected as shown below:

In the Claims:

At Column 8, line 66, "meq./00" should be -- meq./l00 --.

At Column 9, line 36, "an n alkyl" should be -- an alkyl --.

At Column 10, line 2, "smectite having" should be -- smectite clay dispersed in a cosmetically acceptable carrier, said smectite clay having --.

At Column 10, line 21, "carrier" should be -- solvent --.

At Column 10, line 25, "carrier" should be -- solvent --.

At Column 11, line 1, "alcohol phenol," should be -- alcohol, phenol, --.

At Column 11, lines 18-19, "alcohol phenol," should be -- alcohol, phenol, --.

At Column 11, line 36, "alcohol phenol," should be -- alcohol, phenol, --.

At Column 11, line 52, "alcohol phenol," should be -- alcohol, phenol, --.

Signed and Sealed this

First Day of May, 2007

JON W. DUDAS
*Director of the United States Patent and Trademark Office*